United States Patent [19]

Onishi et al.

[11] Patent Number: 4,924,030
[45] Date of Patent: May 8, 1990

[54] PROCESS FOR PREPARING CYCLIC TERPENOIDS

[75] Inventors: Takashi Onishi; Shigeaki Suzuki; Toshiki Mori; Yoshiji Fujita, all of Kurashiki, Japan

[73] Assignee: Kuraray Company Ltd., Kurashiki, Japan

[21] Appl. No.: 164,909

[22] Filed: Mar. 7, 1988

[30] Foreign Application Priority Data

Mar. 17, 1987 [JP] Japan ................................. 62-63417

[51] Int. Cl.$^5$ .......................................... C07C 147/06
[52] U.S. Cl. ..................................................... 568/34
[58] Field of Search ........................................ 568/34

[56] References Cited

FOREIGN PATENT DOCUMENTS 2565974 12/1985 France .
54-119439 9/1979 Japan ................................... 568/28
57-48549 10/1982 Japan .

OTHER PUBLICATIONS

S. Torii et al., Chem. Abstracts, vol. 83, No. 59073t (1975).
J. Am. Chem. Soc., (1984), vol. 106, pp. 3670–3672, "Novel Sysntheis of Acetylenes and Polyenes Via Desulfonylation Reaction", T. Mandai, et al.
J. Org. Chem., (1986), vol. 51, pp. 3834–3838, "Stereo-controlled Synthesis of Vitamin A Through A Double Elimination Reaction. A Novel Convergent $C_{10}+C_{10}$ Route", J. Otera, et al.
Bull. Chem. Soc. Japan., (1985), Vol. 58, pp. 1859–1860, "Electrogenerated Acid–Catalyzed Cyclization of Isoprenoids", Kenji Uneyame, et al.
Chemistry Letters, (1975), vol. 5, pp. 479–482, "Alicyclic Terpenoids From Cyclocitral Phenyl Sulfides. I. Acid--Catalyzed Cyclization of Geranyl Phenyl Sulfides to Cyclocitral Derivatives. A Synthesis of α-And β-Ionones", Sigeru Torii, et al.

Primary Examiner—Mary E. Ceperley
Attorney, Agent, or Firm—Oblon, Spivak, McClelland, Maier & Neustadt

[57] ABSTRACT

A present invention provides a process for preparing a mixture of cyclic terpenoids of general formula (I),

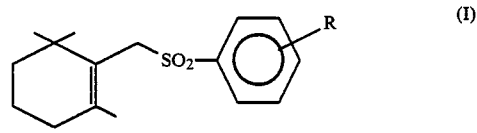

(I)

wherein R is a hydrogen atom or a lower alkyl group, and general formula (II),

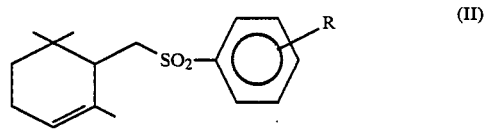

(II)

wherein R is defined as above, containing (I) predominant over (II) by the reaction of an acid with a cyclic terpenoid of general formula (II), or a mixture of cyclic terpenoids of general formulas (I) and (II), containing (II) predominant over (I).

9 Claims, No Drawings

PROCESS FOR PREPARING CYCLIC TERPENOIDS

BACKGROUND OF THE INVENTION (1) Field of the Invention

This invention relates to a process for preparing cyclic terpenoids of general formula (I),

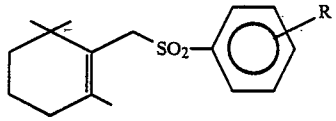

wherein R is a hydrogen atom or a lower alkyl group.

The cyclic terpenoids of general formula (I) are valuable as intermediates for the synthesis of vitamin A acid and vitamin A acetate which are in use of medicines and feed additives. (See Otera et al., J. Am. Chem. Soc., 106, 3670 (1984); Otera et al., J. Org. Chem., 51, 3834 (1986))

(2) Description of the Related Art

It has been reported that cyclic terpenoids are conventionally prepared by the following routes.

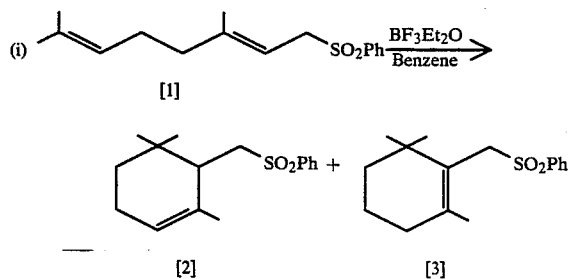

(Yield of [2]+[3] was 93%. The formation ratio of [2]/[3] was 5/1. See Example 8 of Japanese Patent Publication No. 57-48549.)

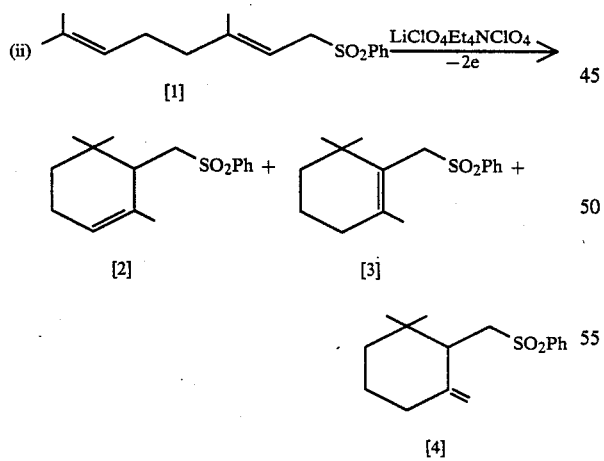

(Yield of [2]+[3]+[4] was 95%. The formation ratio of [2]/[3]/[4] was 86/9/5. See Uneyama et al., Bull. Chem. Soc. Jpn., 58, 1859 (1985).)

The conventional methods of preparing cyclic terpenoids are cyclization reaction of acrylic terpenoids under acidic conditions. As described above, the cyclic terpenoids necessary for the synthesis of vitamin A acid and vitamin A acetate are the compounds of general formula (I) (hereinafter referred to as β-form). The terpenoids prepared by a conventional method contain β-form and also cyclic terpenoids of general formula (II) (hereinafter referred to as α-form) as a by-product.

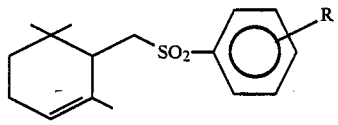

wherein R is the same as defined above. Consequently the yield of β-form at the cyclization becomes low, and a complicated process for the separation of by-product α-form such as silica gel chromatography and the like are needed.

Accordingly, an object of the invention is to provide a process for preparing β-form, the starting material of vitamin A acid and vitamin A acetate, at a good yield in a commercial scale.

Other objects, features and advantages of the invention will become apparent from the following description.

SUMMARY OF THE INVENTION

Accordingly, the present invention provides a process for preparing a mixture of cyclic terpenoids of general formula (I),

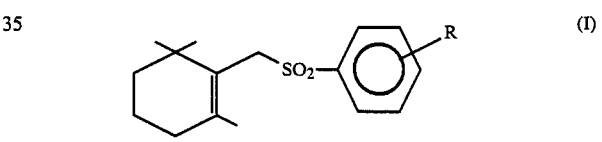

wherein R is hydrogen atom or a lower alkyl group, and general formula (II),

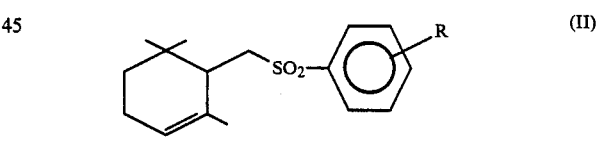

wherein R is the same as defined above, containing the cyclic terpenoid of general formula (I) predominant over (II) by the reaction of an acid and a cyclic terpenoid of of general formula (II) or a mixture of cyclic terpenoids of general formulas (II) and (I), containing the cyclic terpenoid of general formula (II) predominant over (I).

A cyclic terpenoid of general formula (I) can be separated by crystallization from a mixture of cyclic terpenoids of general formulas (I) and (II), containing the cyclic terpenoid of general formula (I) predominant over (II). This mixture of cyclic terpenoids of general formulas (I) and (II), containing the cyclic terpenoid of general formula (I) predominant over (II), can be prepared by the action of an acid with an acyclic terpenoid of general formula (III),

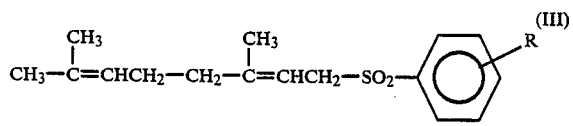

wherein R is a hydrogen atom or a lower alkyl group, and a mixture of cyclic terpenoids of general formulas (I) and

DESCRIPTION OF THE PREFERRED EMBODIMENTS

Referring to the above mentioned general formula (I) (β-form), (II) (α-form) and (III), R is a hydrogen atom or a lower alkyl group, such as methyl, ethyl, n-propyl, i-propyl, n-butyl, i-butyl, t-butyl and the like, which can be substituted at any position of ortho-(o-), meta-(m-), and para-(p-) to sulfonyl group. Among them, more particularly preferable substitutions are hydrogen atom and p-methyl group.

The process of this invention including the separation of β-form by crystallization basically consists of the following two steps.

(1) The operation of preparing a mixture containing β-form predominant over a α-form by the reaction of an acid with α-form, a mixture of a α-form and β-form in which α-form is predominant over β-form, or a mixture of an acyclic terpenoid of general formula (III) with this mixture.

(2) The separation of β-form from the mixture obtained by the operation (1), and the recovery of a mixture of α-form and β-form in which α-form is predominant over β-form from the mother liquor of crystallization.

The mixture of α-form and β-form in which α-form is predominant over β-form recovered from the mother liquor of operation (2), can be converted to a mixture of α-form and β-form in which β-form is predominant over α-form. β-form can be efficiently obtained by recycling these operations.

The mixture of α-form and β-form in which β-form is predominant over a α-form can be prepared by the reaction of an acid and α-form, a mixture of α-form and β-form in which α-form is predominant over β-form, or a mixture of an acyclic terpenoid of general formula (III) and this mixture.

Particularly preferable examples of acids are sulfuric acid; a mixture of sulfuric acid and lower aliphatic carboxylic acids, such as formic acid, acetic acid and the like; inorganic acids except sulfuric acid, such as phosphoric acid and the like; a mixture of sulfuric acid and water; and the like. A preferable amount of acid is in the range of from 0.5 to 20 times, more preferably from 0.3 to 5 times per mole of α-form, the sum of α-form and β-form, or the sum of α-form, β-form and an acyclic terpenoid of general formula (III).

A preferable reaction temperature depending on the type and amount of acid is usually in the range of from −10° C. to 150° C., and a preferable reaction time is in the range of from 1 minute to 10 hours.

Solvents are not necessarily used, but preferably used in case of improving stirring state by decreasing the system viscosity, or facilitating the control of reaction temperature by adding a solvent of low boiling point. Preferable examples of these solvents are hydrocarbons, such as butane, pentane, hexane, heptane, benzene, toluene, xylene, and the like; halogenated hydrocarbons, such as methyl chloride, propyl chloride, methylene dichloride and the like; aliphatic ethers, such as methyl ether, ethyl ether, propyl ether and the like; aliphatic ketones, such as acetone, methyl ethyl ketone, methyl propyl ketone, diisopropyl ketone and the like; esters of aliphatic carboxylic acids, such as methyl acetate, ethyl acetate and the like, as a single or mixed solvent which do not inhibit the reaction. A preferable amount of solvent to acid is practically in the range of from 0.1 to 50 times, more particularly from 0.5 to 30 times by volume.

According to the invention, the ratio of a α-form to β-form, α-form/β-form can be 10–40/90–60 after the reaction with an acid. β-form can be separated by crystallization after the increasing of the ratio of β-form. Preferable solvents for crystallization are aliphatic hydrocarbons, such as hexane, heptane and the like; aromatic hydrocarbons, such as benzene, toluene, xylene and the like; aliphatic ethers, such as ethyl ether, propyl ether and the like; aliphatic alcohols, such as methanol, ethanol, propanol and the like; aliphatic ketones, such as acetone, methyl ethyl ketone and the like; aliphatic carboxylic acids, such as methyl acetate, ethyl acetate and the like; as a single or mixed solvent. A crystallizing temperature depending on the type of solvent is usually in the range of from the reflux temperature to −50° C. An amount of solvent is used in the range of from 0.1 to 200 times by volume to the sum of α-form and β-form. Although the separation of α-form and β-form by crystallization can be conducted without solvent, but generally the use of solvent contributes to get high purity β-form. The crystallization can be conducted under high pressure.

The mother liquor separated from β-form, distilled off the solvent when used under normal pressure or reduced pressure, provides a mixture of α-form and β-form in which α-form is predominant over β-form. The obtained mixture, mixed with a α-form, or further mixed with an acyclic terpenoid of general formula (III) can be transformed to a mixture of α-form and β-form in which β-form is predominant over α-form by the reaction of an acid, and can be used for the separation of β-form by crystallization. The recycling of these operations provides practically β-form only efficiently in commercial scale production. The mother liquor can be used untouched or after the removal of high boiling part by molecular distillation and the like.

EXAMPLES

The present invention will now be described with reference to the following examples.

EXAMPLE 1

In a three neck flask of 300 ml capacity, 32.1 g (17.5 ml) of concentrated sulfuric acid, 18.4 g (17.5 ml) of acetic acid and 50 ml of pentane were placed. To the mixture, 71.5 g (purity 83%, net 59.3 g) of the mixture of α-cyclogeranyl phenyl sulfone [2] and β-cyclogeranyl phenyl sulfone [3], the ratio of [2]/[3] being 54/46, and 100 ml of pentane were added over a period of 5 minutes at room temperature under vigorous stirring. The inside temperature raised up to 38° C. After 5 minutes, the reaction mixture was poured into a mixture of ice and ethyl acetate (300 g and 300 ml each). The cooled water, washed the flask successively two times, was added and then the reaction mixture was extracted with 300 ml of ethyl acetate. The organic layer was separated and washed successively with 500 ml of water, and 300 ml of a 10% sodium bicarbonate aqueous solution and then dried over magnesium sulfate. Magnesium sulfate was separated by filtration, and then the solvent was removed by distillation to give 69.1 g (purity 85.5%, net 59.1 g) of a yellowish brown viscous oil. The ratio of [2] and [3], [2]/[3] of the oil was found to be 29/71 by gas chromatography.

Gas chromatography conditions:
Column, Thermon 1000, 1 m,
Column temperature 150–250° C.,
Progressive rate 16° C./minute.

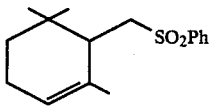

α-cyclogeranyl phenyl sulfone [2]

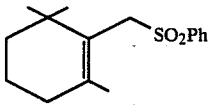

β-cyclogeranyl phenyl sulfone [3]

Thus obtained viscous oil was dissolved in 300 ml of a mixed solution of hexane and benzene (volume ratio of hexane/benzene was 97/3) at reflux, and gradually cooled and then kept for 5 hours at 10° C. The deposited crystal was filtered with a glass filter to give 30.9 g of white crystal. The obtained crystal was found to ba a mixture of [2] and [3], the ratio of [2]/[3] being 5.0/95.0.

The solvent in mother liquor after crystallization was subjected to distillation under reduced pressure to give 33.7 g (purity 83.7%, net 28.8 g) of viscous oil. The obtained product was found a mixture of [2] and [3], the ratio of [2]/[3] being 55.3/44.7 by gas chromatography.

In a three neck flask of 200 ml capacity, 15.3 g (8.3 ml) of concentrated sulfuric acid, 8.8 g (8.3 ml) of acetic acid, and 24 ml of pentane were placed.

To the mixture, 33.7 g (purity 83.7%, net 28.2 g, the ratio of [2]/[3]=55.3/44.7) of viscous oil recovered from the mother liquor after crystallization and 48 ml of pentane were added over a period of 5 minutes at room temperature under vigorous stirring. After 5 minutes, the reaction mixture was poured into a mixture of ice and ethyl acetate (50 g. and 50 ml each). The same procedure was repeated as described above, and extracted. The solvent was removed by distillation to give 32.5 g of brown viscous oil (purity 84.0%, net 27.3 g). The ratio of [2] and [3], [2]/[3] of the oil was found 27.2/72.8 by gas chromatography.

The obtained mixture was dissolved in 150 ml of a mixed solution of haxane and benzene (volume ratio of hexane/benzene was 97/3) at reflux, and the same procedure was repeated as described above, and 14.1 g of crystal was obtained. The crystal was found to be a mixture of [2] and [3], the ratio of [2]/[3] being 4.2/95.8. The solvent in mother liquor after crystallization was removed by distillation under reduced pressure to give 15.4 g of brown viscous oil (purity 85.7%, net 13.2 g). The obtained product was found a mixture of [2] and [3], the ratio of [2]/[3] being 51.8/48.2 by gas chromatography.

EXAMPLE 2

To 15.4 g (purity 85.7%, net 13.2 g, [2]/[3]=51.8/48.2) of brown viscous oil obtained by Example 1, 30.0 g (net 27.1 g) of geranyl phenyl sulfone (purity 90.3%) was mixed. To the mixture of 21.3 g of concentrated sulfuric acid, 12.2 g of acetic acid, and 35 ml of pentane, thus obtained mixture was added with 70 ml of pentane for a period of 3 minutes, at room temperature under vigorous stirring. After 5 minutes, the reaction mixture was poured into a mixture of ice and ethyl acetate (300 g and 300 ml each). The same procedure as described in Example 1 was repeated, and then 43.1 g (purity 86.5%, net 37.3 g) of brown viscous oil was obtained removing the solvent by distillation under reduced pressure. The ratio of [2] and [3], [2]/[3] of this obtained oil was found 23.7/76.3 by gas chromatography. The obtained oil was dissolved in 250 ml of hexane at reflux, and cooled to room temperature, and kept for 24 hours at room temperature. The deposited white crystal was filtered by a glass filter, and 22.5 g of crystal was obtained. The obtained crystal was a mixture of [2] and [3], the ratio of [2]/[3] being 4.8/95.2. The solvent in the mother liquor after crystallization was removed by distillation under reduced pressure to give 16.5 g (purity 89.7% net 14.8 g) brown viscous oil. The obtained product was found a mixture of [2] and [3], the ratio of [2]/[3] being 52.4/47.6 by gas chromatography.

EXAMPLE 3

In a three neck flask of 200 ml capacity, 10.0 g of concentrated sulfuric acid and 30 ml of hexane were placed and stirred vigorously. To this mixture, 26.8 g (purity 74%, net 19.8 g) of a mixture of α-cyclogeranyl p-tolyl sulfone [5] and β-cyclogeranyl p-tolyl sulfone [6], the ratio of [5] and [6], [5]/[6] being 69/31, and 30 ml of hexane were quickly dropped at 30° C. and vigorously stirred at 35°–40° C. of inside temperature. To the reaction mixture, 50 ml of iced water was poured, stirred for a period of 5 minutes, and transferred to a separation funnel, followed by the extraction with 200 ml of ethyl acetate. The organic layer was washed with 100 ml of a 5% sodium bisulfate aqueous solution, and then with 100 ml of water successively. The solvent and other compounds of low boiling point were removed by a evaporator to give 21.2 g (purity 83%, net 17.0 g). The ratio of [5] and [6] of the obtained mixture, [5]/[6] was 23/77 by gas chromatography.

Gas chromatography conditions:
Column, Thermon 1000, 1 m,
Column temperature 150–250° C.,
Progressive rate 16° C./minute.

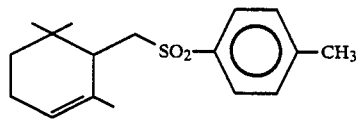

α-cyclogeranyl p-tolyl sulfone [5]

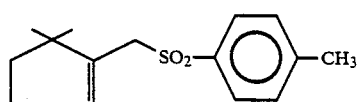

-continued

β-cyclogeranyl p-tolyl sulfone [6]

The obtained brown viscous oil (21.2 g) was dissolved in 200 mol of hexane at reflux, and gradually cooled and kept for 20 hours at room temperature. The deposited white crystal was filtered with a glass filter, and 11.5 g of crystal was obtained. The obtained crystal was a mixture of [5] and [6], the ratio of [5]/[6] being 5/95. The solvent in the mother liquor after crystallization was removed by distilation under reduced pressure to give 7.2 g (purity 85%, net 6.1 g) of brown viscous oil. The ratio of [5] and [6], [5]/[6] being 56.9/43.1 was found by gas chromatography.

EXAMPLES 4–10

The same procedure of Example 1 was repeated except that a mixture (the ratio of [2] and [3], [2]/[3]=65.13/34.87, purity 68.48%) was used in sulfuric acid-acetic acid system, wherein the volume of acetic acid was the same of that of concentrated sulfuric acid, and the volume of pentane was 5 times of that of acetic acid. The results are shown as in the following table.

| Example No. | Mole Ratio of $H_2SO_4$/ ([2] + [3]) | Reaction Time (min.) | Reaction Temperature (°C.) | Recovery of ([2] + [3]) (%) | Ratio of ([2]/[3]) |
|---|---|---|---|---|---|
| 4 | 2.19 | 5 | 30–35 | 95.82 | 29.00/71.00 |
| 5 | 2.19 | 15 | 30–35 | 92.28 | 26.38/73.62 |
| 6 | 2.19 | 30 | 30–35 | 89.71 | 25.40/74.60 |
| 7 | 1.50 | 15 | 30–40 | 95.53 | 29.50/70.50 |
| 8 | 1.50 | 60 | 30–40 | 93.76 | 26.34/73.64 |
| 9 | 1.00 | 60 | 30–35 | 98.71 | 29.21/70.78 |
| 10 | 1.00 | 60 | 40–45 | 97.23 | 28.45/71.55 |

EXAMPLES 11–14

The same procedure of Example 1 was repeated except that a mixture of [2] and [3] (the ratio of [2]/[3]=63.9/36.1, purity 65.6%) were used in sulfuric acid-water system, wherein the volume ratio of water to sulfuric acid was 0.3 time, that of pentane to sulfuric acid was 17 times. The results are shown as in the following table.

| Example No. | Mole Ratio of $H_2SO_4$/ ([2] + [3]) | Reaction Time (hr.) | Reaction Temperature (°C.) | Recovery of ([2] + [3]) (%) | Ratio of ([2]/[3]) |
|---|---|---|---|---|---|
| 11 | 0.9 | 1 | 37–38 | 96.98 | 33.5/66.6 |
| 12 | 1.1 | 1 | 37–38 | 92.40 | 31.7/68.3 |
| 13 | 0.9 | 5 | 20–25 | 96.1 | 14.4/85.6 |
| 14 | 0.9 | 5 | 20–25 | 95.1 | 16.5/83.5 |

What is claimed is:

1. A process for preparing a mixture of cyclic terpenoids of formula (I),

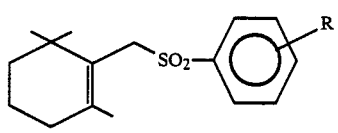 (I)

wherein R is a hydrogen atom or a lower alkyl group, and formula (II),

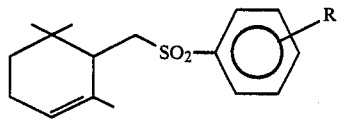 (II)

wherein R is defined as above, containing the cyclic terpenoid of formula (I) predominant over (III), which comprises reacting an acid selected from the group consisting of sulfuric acid, a mixture of sulfuric acid and a lower aliphatic carboxylic acid, and a mixture of sulfuric acid and water, with a cyclic terpenoid of formula (II), or a mixture of cyclic terpenoids of formulas (I) and (II), containing the cyclic terpenoid of formula (II) predominant over (I), in a hydrocarbon solvent.

2. A process for preparing a cyclic terpenoid, which comprises the steps:

(1) reacting an acid selected from the group consisting of sulfuric acid, a mixture of sulfuric acid and a lower aliphatic carboxylic acid, and a mixture of sulfuric acid and water, with a cyclic terpenoid of formula (II),

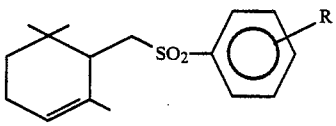 (II)

wherein R is a hydrogen atom or a lower alkyl group, or a mixture of cyclic terpenoids of formula (I),

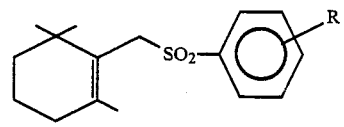 (I)

wherein R is defined as above, and formula (II), containing the cyclic terpenoid of formula (II) predominant over (I), in a hydrocarbon solvent; and (2) separating a cyclic terpenoid of formula (I) by crystallization from a mixture of cyclic terpenoids of formulas (I) and (II), containing (I) predominant over (II), obtained in step (1).

3. A process according to claim 2, further comprising the step of reacting an acid with a mixture of cyclic terpenoids of formulas (I) and (II), containing (II) predominant over (I), which is recovered from the mother liquor after said crystallization, and then there separating the cyclic terpenoid of formula (I) by crystallization.

4. A process according to claim 2, further comprising the step of recycling a mixture of cyclic terpenoids of formulas (I) and (II), containing (II) predominant over (I), which is recovered from the mother liquor after crystallization with or without the solvent, to the step of reacting an acid with a mixture of cyclic terpenoids of formulas (I) and (II), containing (II) predominant over (I).

5. A process for preparing a cyclic terpenoid, which comprises the steps:

(1) reacting an acid selected from the group consisting of sulfuric acid, a mixture of sulfuric acid and a lower aliphatic carboxylic acid, and a mixture of sulfuric acid and water, with a mixture of an acyclic terpenoid of formula (III),

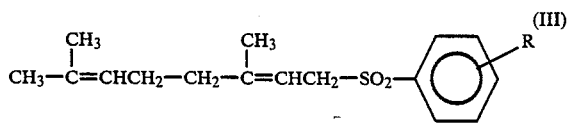
(III)

wherein R is a hydrogen atom or a lower alkyl group, and cyclic terpenoids of formula (I) and (II), containing (II) predominant over (I),

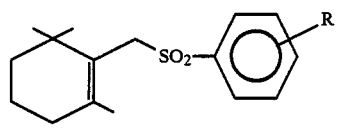
(I)

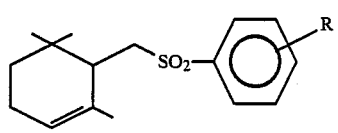
(II)

wherein R is defined as above, in a hydrocarbon solvent; and (2) separating a cyclic terpenoid of formula (I) by crystallization from a mixture of cyclic terpenoids of formulas (I) and (II), containing (I) predominant over (II), obtained in step (1).

6. A process according to claim 5, further comprising the step of reacting an acid with a mixture of cyclic terpenoids of formulas (I) and (II), containing (II) predominant over (I), recovered from the mother liquor after crystallization, or a mixture of the mixture and an acyclic terpenoid of formula (III).

7. A process according to claim 5, further comprising the step of recycling a mixture of cyclic terpenoids of formulas (I) and (II), containing (II) predominant over (I), recovered from the mother liquor after crystallization with or without the solvent, to the step of reacting an acid with the mixture of an acyclic terpenoid of formula (III) and cyclic terpenoids of general formulas (I) and (II).

8. A process according to claim 1, 2, or 5, wherein the reaction is conducted in the range of from −10° C. to 150° C.

9. A process according to claim 2 or 5, wherein the crystallization solvent is selected from the group consisting of of aliphatic hydrocarbons, aromatic hydrocarbons, aliphatic ethers, aliphatic alcohols, aliphatic ketones, and esters of aliphatic carboxylic acids.

* * * * *